United States Patent
Zhang et al.

(10) Patent No.: US 9,345,764 B2
(45) Date of Patent: *May 24, 2016

(54) MOESIN MODULATORS AND USES THEREOF

(75) Inventors: Yue Zhang, Shanghai (CN); Jun Bao, Shanghai (CN); Hua Mao, Shanghai (CN); Zhinan Shou, Shanghai (CN); Weina Situ, Shanghai (CN)

(73) Assignee: SHANGHAI KEXIN BIOTECH CO., LTD., Shanghai (CN)

( * ) Notice: Subject to any disclaimer, the term of this patent is extended or adjusted under 35 U.S.C. 154(b) by 26 days.

This patent is subject to a terminal disclaimer.

(21) Appl. No.: 13/878,232

(22) PCT Filed: Oct. 8, 2011

(86) PCT No.: PCT/CN2011/080520
§ 371 (c)(1),
(2), (4) Date: Apr. 8, 2013

(87) PCT Pub. No.: WO2012/045274
PCT Pub. Date: Apr. 12, 2012

(65) Prior Publication Data
US 2013/0266537 A1    Oct. 10, 2013

(30) Foreign Application Priority Data
Oct. 8, 2010   (WO) ................ PCT/CN2010/077589

(51) Int. Cl.
| C07K 7/08 | (2006.01) |
| A61K 38/08 | (2006.01) |
| A61K 38/20 | (2006.01) |
| A61K 45/06 | (2006.01) |
| A61K 38/19 | (2006.01) |
| A61K 38/10 | (2006.01) |
| C07K 7/06 | (2006.01) |
| A61K 39/395 | (2006.01) |
| C07K 16/18 | (2006.01) |
| C07K 16/28 | (2006.01) |

(52) U.S. Cl.
CPC ............ *A61K 39/3955* (2013.01); *A61K 38/08* (2013.01); *A61K 38/10* (2013.01); *A61K 38/191* (2013.01); *A61K 38/204* (2013.01); *A61K 38/2006* (2013.01); *A61K 38/2086* (2013.01); *A61K 45/06* (2013.01); *C07K 7/06* (2013.01); *C07K 7/08* (2013.01); *C07K 16/18* (2013.01); *C07K 16/28* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 5,976,810 A | 11/1999 | Wagatsuma et al. |
| 6,225,442 B1 | 5/2001 | Wagatsuma et al. |
| 2010/0068742 A1* | 3/2010 | Alessi et al. .................... 435/15 |
| 2013/0203091 A1 | 8/2013 | Zhang et al. |
| 2013/0244259 A1 | 9/2013 | Suzuki et al. |
| 2013/0266537 A1 | 10/2013 | Zhang et al. |
| 2013/0316379 A1 | 11/2013 | Zhang et al. |

FOREIGN PATENT DOCUMENTS

| CA | 2199498 A1 | 3/1996 |
| EP | 2624854 A1 | 8/2013 |
| EP | 2624855 A1 | 8/2013 |
| EP | 2624856 A1 | 8/2013 |
| JP | 3467040 B | 11/2003 |
| JP | 3735676 B1 | 1/2006 |
| JP | 2013-541538 A | 11/2013 |
| JP | 2014-503467 A | 2/2014 |
| WO | 9607914 A1 | 3/1996 |
| WO | 2006/015079 A2 | 2/2006 |
| WO | 2008122789 A2 | 10/2008 |
| WO | 2012039161 A1 | 3/2012 |
| WO | 2012045273 A1 | 4/2012 |
| WO | 2012045274 A1 | 4/2012 |
| WO | 2012045275 A1 | 4/2012 |
| WO | 2012045279 A1 | 4/2012 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Espinoza et al., "Anti-moesin antibodies derived from patients with aplastic anemia stimulate monocytic cells to secrete TNF-a through an ERK1/2-dependent pathway" Intl. Immu. 21 (8): 913-923 (2009).
Hipfner et al., "Slik Sterile-20 kinase regulates Moesin activity to promote epithelial integrity during tissue growth" Genes Dev. 18:2243-2248 (2004).
Lankes et al., "A heparin-binding protein involved in inhibition of smooth-muscle cell proliferation" Biochem. J. 251:831-842 (1988).
Louvet-Vallee, "ERM proteins: From cellular architecture to cell signaling" Biol. Cell 92:305-316 (2000).
Oshiro et al., "Phosphorylation of Moesin by Rho-associated Kinase (Rho-kinase) Plays a Crucial Role in the Formation of Microvilli-like Structures" J. Biol. Chem. 273:34663-34666 (1998).
Pearson et al., "Structure of the ERM Protein Moesin Reveals the FERM Domain Fold Masked by an Extended Actin Binding Tail Domain" Cell 101:259-270 (2000).
Sato et al., "A gene family consisting of ezrin, radixin and moesin. Its specific localization at actin filament/plasma membrane association sites" J. Cell Sci. 103:131-143 (1992).
Takahashi et al., "Direct Interaction of the Rho GDP Dissociation Inhibitor with Ezrin/Radixin/Moesin Initiates the Activation of the Rho Small G Protein" J. Biol. Chem. 272:23371-23375 (1997).

(Continued)

*Primary Examiner* — Brian J Gangle
*Assistant Examiner* — Andrea McCollum
(74) *Attorney, Agent, or Firm* — Jun He Law Offices P.C.; Zhaohui Wang

(57) ABSTRACT

The present application provides compositions and methods useful for treating and diagnosing diseases and disorders associated with moesin activation.

11 Claims, 7 Drawing Sheets

(56) References Cited

OTHER PUBLICATIONS

Takamatsu et al., "Specific antibodies to moesin, a membrane-cytoskeleton linker protein, are frequently detected in patients with acquired aplastic anemia" Blood 109:2514-2520 (2007).
Takamatsu et al., "Anti-Moesin Antibodies in the Serum of Patients with Aplastic Anemia Stimulate Peripheral Blood Mononuclear Cells to Secrete TNF-α and IFN-γ" J. Immunol. 182:703-710 (2009).
Tohme et al., "Moesin Functions as a Lipopolysaccharide Receptor on Human Monocytes" Infect. Immun. 67(7): 3215-3220 (1999).
Wagatsuma et al., "Ezrin, radixin and moesin are possible autoimmune antigens in rheumatoid arthritis" Mol. Immunol. 33(15):1171-1176 (1996).
Wu Ming, et al., "Expression and significance of moesin in human astrocytomas" Chinese Journal of Neurosurgical Disease Research. 9 (1): 15-18 (2010).
Edwards et al., "The 2.7 Å Crystal Structure of the Activated FERM Domain of Moesin: An Analysis of Structural Changes on Activation" Biochemistry 40: 7061-7068 (2001).
Finnerty et al., "The EBP50-moesin interaction involves a binding site regulated by direct masking on the FERM domain" J. Cell Science 117:1547-1552 (2004).
"ISR and Written Opinion of PCT/CN2011/080520", (Jan. 19, 2012).
Jeon Songhee et al.:"RhoA and Rho Kinase-dependent Phosphorylation of Moesin at Thr-558 in Hippocampal Neuronal Cells by Glutamate" J.Biol. Chern 277: 16576-16584 (2002).
Alissa Routhier et al.: "Pharmacological inhibition of Rho-kinase signaling with Y-27632 blocks melanoma tumor growth" Oncology Reports 23: 861-867 (2010).
Okayama Tohunari et al.:"Attenuated response to liver injury in moesin-deficient mice: Impaired stellate cell migration and decreased fibrosis" BIO 1782: 542-548 (2008).
Ana Estecha et al.: "Moesin orchestrates cortical polarity of melanoma tumour cells to initiate 3D invasion" Journal of Cell Science 122: 3492-3501 (2009).
Martin Hennenberg et al.: "Intrahepatic Hyperphosphorylation of the Rho-Kinase-Substrate Moesin in Experimental and Human Cirrhosis" Gastroenterolofy, vol. 130, No. 4, Suppl. 2, p. A669, XP009175910, (2006).
Li Meng-tao et al.:"Human pulmonary microvascular endothelial cells injury could be mediated by the co-effect of moesin and anti-moesin antibody" Chin J Rheumatol, Apr. 2010, vol. 214, No. 4, p. 232-235.

"ISR and Written Opinion of PCT CN2011/080519", Completed: Jan. 4, 2012.
Pedro L et al.: "Development of a high-throughout AlphaScreen assay measuring full-length LRRK2(G2019S) kinase activity using moesin protein substrate" Analytical Biochemistry 404: 45-51 (2010).
Zhirong Qi et al.: "Autoantibodies specific to hnRNP K: a new diagnostic marker for immune pathophysiology in aplastic anemia" Ann Hematol 89: 1255-1263 (2010).
"ISR and Written Opinion of PCT CN2011/080523", Completed Jan. 4, 2012.
Pang Yan et al., "Study on the expression of interferon-gamma and tumor necrosis factor-α in peripheral blood of patients with chronic aplastic anemia" Journal of Clinical Hematology, 23 (7): 416-418 (Jul. 2010).
Shcherbina et al., "Moesin, the major ERM protein of lymphocytes and platelets, differs from ezrin in its insensitivity to calpain" FEBS Letters 443:31-36 (1999).
Young et al., "Current concepts in the pathophysiology and treatment of aplastic anemia" Blood, 108:2509-2519 (2006).
"ISR and Written Opinion of PCT CN2011/080532", Completed Jan. 4, 2012.
Hiroyuki Takamatsu, et al., "Anti-Moesin Antibodies in the Serum of Patients with Aplastic Anemia Stimulate Peripheral Blood Mononuclear Cells to Secrete INF- and IFN-" (2009).
Yue Zhang et al., "Autoantibodies Directed Against Moesin C471-577/N1-297 Are Novel and Specific Biomarkers of Immune Thrombocytopenic Purpura (ITP)" (2011).
"ISR and Written Opinion of PCT CN2011/080538", Completed Jan. 5, 2012.
Alarcon-Segovia, D. et al., "Antiphospholipid antibodies and the antiphospholipid syndrome in systemic lupus erythematosus. A prospective analysis of 500 consecutive patients" Medicine 68 (6): 353-365 (1989).
Asherson, R.A., et al., "The "Primary" Antiphospholipid Syndrome: Major Clinical and Serological Features" Medicine 68 (6): 366-374 (1989).
Nakamura Fumihiko et al., "Phosphorylation of Threonine 558 in the Carboxyl-terminal Actin-binding Domain of Moesin by Thrombin Activation of Human Platelets" Biological Chemistry 270: 52(1995).
ZhaoJiuLiang "Study on Anti-moesin Antibodies in Patients with Connective Tissue Diseases" Jun. 1, 2009.

* cited by examiner

Amino Acid Sequence of the Full Length Human Moesin Protein

MPKTISVRVT TMDAELEFAI QPNTTGKQLF DQVVKTIGLR EVWFFGLQYQ
DTKGFSTWLK LNKKVTAQDV RKESPLLFKF RAKFYPEDVS EELIQDITQR
LFFLQVKEGI LNDDIYCPPE TAVLLASYAV QSKYGDFNKE VHKSGYLAGD
KLLPQRVLEQ HKLNKDQWEE RIQVWHEEHR GMLREDAVLE YLKIAQDLEM
YGVNYFSIKN KKGSELWLGV DALGLNIYEQ NDRLTPKIGF PWSEIRNISF
NDKKFVIKPI DKKAPDFVFY APRLRINKRI LALCMGNHEL YMRRRKPDTI
EVQQMKAQAR EEKHQKQMER AMLENEKKKR EMAEKEKEKI EREKEELMER
LKQIEEQTKK AQQELEEQTR RALELEQERK RAQSEAEKLA KERQEAEEAK
EALLQASRDQ KKTQEQLALE MAELTARISQ LEMARQKKES EAVEWQQKAQ
MVQEDLEKTR AELKTAMSTP HVAEPAENEQ DEQDENGAEA SADLRADAMA
KDRSEEERTT EAEKNERVQK HLKALTSELA NARDESKKTA NDMIHAENMR
LGRDKYKTLR QIRQGNTKQR IDEFESM (SEQ ID NO.3)

Figure 1(a)

cDNA Sequence encoding for the Full Length Human Moesin Protein

ATGCCCAAAACGATCAGTGTGCGTGTGACCACCATGGATGCAGAGCTGGAGTTTGCCATCCAGC
CCAACACCACCGGGAAGCAGCTATTTGACCAGGTGGTGAAAACTATTGGCTTGAGGGAAGTTTG
GTTCTTTGGTCTGCAGTACCAGGACACTAAAGGTTTCTCCACCTGGCTGAAACTCAATAAGAAG
GTGACTGCCCAGGATGTGCGGAAGGAAAGCCCCCTGCTCTTTAAGTTCCGTGCCAAGTTCTACC
CTGAGGATGTGTCCGAGGAATTGATTCAGGACATCACTCAGCGCCTGTTCTTTCTGCAAGTGAA
AGAGGGCATTCTCAATGATGATATTTACTGCCCGCCTGAGACCGCTGTGCTGCTGGCCTCGTAT
GCTGTCCAGTCTAAGTATGGCGACTTCAATAAGGAAGTGCATAAGTCTGGCTACCTGGCCGGAG
ACAAGTTGCTCCGCAGAGAGTCCTGGAACAGCACAAACTCAACAAGGACCAGTGGGAGGAGCG
GATCCAGGTGTGGCATGAGGAACACCGTGGCATGCTCAGGGAGGATGCTGTCCTGGAATATCTG
AAGATTGCTCAAGATCTGGAGATGTATGGTGTGAACTACTTCAGCATCAAGAACAAGAAAGGCT
CAGAGCTGTGGCTGGGGTGGATGCCCTGGGTCTCAACATCTATGAGCAGAATGACAGACTAAC
TCCCAAGATAGGCTTCCCCTGGAGTGAAATCAGGAACATCTCTTTCAATGATAAGAAATTTGTC
ATCAAGCCCATTGACAAAAAAGCCCCGGACTTCGTCTTCTATGCTCCCCGGCTGCGGATTAACA
AGCGGATCTTGGCCTTGTGCATGGGGAACCATGAACTATACATGCGCCGTCGCAAGCCTGATAC
CATTGAGGTGCAGCAGATGAAGGCACAGGCCCGGGAGGAGAAGCACCAGAAGCAGATGGAGCGT
GCTATGCTGGAAAATGAGAAGAAGAAGCGTGAAATGGCAGAGAAGGAGAAAGAGAAGATTGAAC
GGGAGAAGGAGGAGCTGATGGAGAGGCTGAAGCAGATCGAGGAACAGACTAAGAAGGCTCAGCA
AGAACTGGAAGAACAGACCCGTAGGGCTCTGGAACTTGAGCAGGAACGGAAGCGTGCCCAGAGC
GAGGCTGAAAAGCTGGCCAAGGAGCGTCAAGAAGCTGAAGAGGCCAAGGAGGCCTTGCTGCAGG
CCTCCCGGGACCAGAAAAAGACTCAGGAACAGCTGGCCTTGGAAATGGCAGAGCTGACAGCTCG
AATCTCCCAGCTGGAGATGGCCCGACAGAAGAAGGAGAGTGAGGCTGTGGAGTGGCAGCAGAAG
GCCCAGATGGTACAGGAAGACTTGGAGAAGACCCGTGCTGAGCTGAAGACTGCCATGAGTACAC
CTCAT<u>GTGGCAGAGCCTGCTGAGAATGAGCAGGATGAGCAGGATGAGAATGGGGCAGAGGCTAG</u>
<u>TGCTGACCTACGGGCTGATGCTATGGCCAAGGACCGCAGTGAGGAGGAACGTACCACTGAGGCA</u>
<u>GAGAAGAATGAGCGTGTGCAGAAGCACCTGAAGGCCCTCACTTCGGAGCTGGCCAATGCCAGAG</u>
<u>ATGAGTCCAAGAAGACTGCCAATGACATGATCCATGCTGAGAACATGCGACTGGGCCGAGACAA</u>
<u>ATACAAGACCCTGCGCCAGATCCGGCAGGGCAACACCAAGCAGCGCATTGACGAATTTGAGTCT</u>
<u>ATGTAA</u>  (SEQ ID NO:4)

Figure 1(b)

pET32a(+)

pET28a(+)

SEQUENCE LISTING

```
<160> NUMBER OF SEQ ID NOS: 4

<210> SEQ ID NO 1
<211> LENGTH: 107
<212> TYPE: PRT
<213> ORGANISM: Artificial
<220> FEATURE:
<223> OTHER INFORMATION: C-terminal tail domain of human moesin

<400> SEQUENCE: 1

His Val Ala Glu Pro Ala Glu Asn Glu Gln Asp Glu Gln Asp Glu Asn
1               5                   10                  15

Gly Ala Glu Ala Ser Ala Asp Leu Arg Ala Asp Ala Met Ala Lys Asp
            20                  25                  30

Arg Ser Glu Glu Glu Arg Thr Thr Glu Ala Glu Lys Asn Glu Arg Val
        35                  40                  45

Gln Lys His Leu Lys Ala Leu Thr Ser Glu Leu Ala Asn Ala Arg Asp
    50                  55                  60

Glu Ser Lys Lys Thr Ala Asn Asp Met Ile His Ala Glu Asn Met Arg
65                  70                  75                  80

Leu Gly Arg Asp Lys Tyr Lys Thr Leu Arg Gln Ile Arg Gln Gly Asn
                85                  90                  95

Thr Lys Gln Arg Ile Asp Glu Phe Glu Ser Met
            100                 105

<210> SEQ ID NO 2
<211> LENGTH: 13
<212> TYPE: PRT
<213> ORGANISM: Artificial
<220> FEATURE:
<223> OTHER INFORMATION: Amino acid residues surrounding the Thr558 site
```

```
<400> SEQUENCE: 2

Gly Arg Asp Lys Tyr Lys Thr Leu Arg Gln Ile Arg Gln
1               5                   10

<210> SEQ ID NO 3
<211> LENGTH: 577
<212> TYPE: PRT
<213> ORGANISM: Artificial
<220> FEATURE:
<223> OTHER INFORMATION: The full length human moesin protein

<400> SEQUENCE: 3

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Ala Leu Cys Met Gly Asn His
        275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Met Glu Arg
305                 310                 315                 320

Ala Met Leu Glu Asn Glu Lys Lys Lys Arg Glu Met Ala Glu Lys Glu
                325                 330                 335
```

-continued

```
Lys Glu Lys Ile Glu Arg Glu Lys Glu Leu Met Glu Arg Leu Lys
            340                 345                 350
Gln Ile Glu Glu Gln Thr Lys Lys Ala Gln Gln Glu Leu Glu Gln
            355                 360                 365
Thr Arg Arg Ala Leu Glu Leu Glu Gln Glu Arg Lys Arg Ala Gln Ser
370                 375                 380
Glu Ala Glu Lys Leu Ala Lys Glu Arg Gln Glu Ala Glu Ala Lys
385                 390                 395                 400
Glu Ala Leu Leu Gln Ala Ser Arg Asp Gln Lys Lys Thr Gln Glu Gln
            405                 410                 415
Leu Ala Leu Glu Met Ala Glu Leu Thr Ala Arg Ile Ser Gln Leu Glu
            420                 425                 430
Met Ala Arg Gln Lys Lys Glu Ser Glu Ala Val Glu Trp Gln Gln Lys
            435                 440                 445
Ala Gln Met Val Gln Glu Asp Leu Glu Lys Thr Arg Ala Glu Leu Lys
            450                 455                 460
Thr Ala Met Ser Thr Pro His Val Ala Glu Pro Ala Glu Asn Glu Gln
465                 470                 475                 480
Asp Glu Gln Asp Glu Asn Gly Ala Glu Ala Ser Ala Asp Leu Arg Ala
            485                 490                 495
Asp Ala Met Ala Lys Asp Arg Ser Glu Glu Glu Arg Thr Thr Glu Ala
            500                 505                 510
Glu Lys Asn Glu Arg Val Gln Lys His Leu Lys Ala Leu Thr Ser Glu
            515                 520                 525
Leu Ala Asn Ala Arg Asp Glu Ser Lys Lys Thr Ala Asn Asp Met Ile
            530                 535                 540
His Ala Glu Asn Met Arg Leu Gly Arg Asp Lys Tyr Lys Thr Leu Arg
545                 550                 555                 560
Gln Ile Arg Gln Gly Asn Thr Lys Gln Arg Ile Asp Glu Phe Glu Ser
            565                 570                 575
Met
```

<210> SEQ ID NO 4
<211> LENGTH: 1734
<212> TYPE: DNA
<213> ORGANISM: Artificial
<220> FEATURE:
<223> OTHER INFORMATION: cDNA Sequence encoding for the Full Length
      Human Moesin Protein

<400> SEQUENCE: 4

| | | | | | |
|---|---|---|---|---|---|
| atgcccaaaa | cgatcagtgt | gcgtgtgacc | accatggatg | cagagctgga | gtttgccatc | 60 |
| cagcccaaca | ccaccgggaa | gcagctattt | gaccaggtgg | tgaaaactat | tggcttgagg | 120 |
| gaagtttggt | tctttggtct | gcagtaccag | gacactaaag | gtttctccac | ctggctgaaa | 180 |
| ctcaataaga | aggtgactgc | ccaggatgtg | cggaaggaaa | gcccctgct | ctttaagttc | 240 |
| cgtgccaagt | tctaccctga | ggatgtgtcc | gaggaattga | ttcaggacat | cactcagcgc | 300 |
| ctgttctttc | tgcaagtgaa | agagggcatt | ctcaatgatg | atatttactg | cccgcctgag | 360 |
| accgctgtgc | tgctggcctc | gtatgctgtc | cagtctaagt | atggcgactt | caataaggaa | 420 |
| gtgcataagt | ctggctacct | ggccggagac | aagttgctcc | cgcagagagt | cctggaacag | 480 |
| cacaaactca | acaaggacca | gtgggaggag | cggatccagg | tgtggcatga | ggaacaccgt | 540 |
| ggcatgctca | gggaggatgc | tgtcctggaa | tatctgaaga | ttgctcaaga | tctggagatg | 600 |
| tatggtgtga | actacttcag | catcaagaac | aagaaaggct | cagagctgtg | gctgggggtg | 660 |

-continued

```
gatgccctgg gtctcaacat ctatgagcag aatgacagac taactcccaa gataggcttc    720
ccctggagtg aaatcaggaa catctctttc aatgataaga aatttgtcat caagcccatt    780
gacaaaaaag ccccggactt cgtcttctat gctccccggc tgcggattaa caagcggatc    840
ttggccttgt gcatgcggaa ccatgaacta tacatgcgcc gtcgcaagcc tgataccatt    900
gaggtgcagc agatgaaggc acaggcccgg gaggagaagc accagaagca gatggagcgt    960
gctatgctgg aaaatgagaa gaagaagcgt gaaatggcag agaaggagaa agagaagatt   1020
gaacgggaga aggaggagct gatggagagg ctgaagcaga tcgaggaaca gactaagaag   1080
gctcagcaag aactggaaga acagacccgt agggctctgg aacttgagca ggaacggaag   1140
cgtgcccaga gcgaggctga aaagctggcc aaggagcgtc aagaagctga agaggccaag   1200
gaggccttgc tgcaggcctc ccgggaccag aaaaagactc aggaacagct ggccttggaa   1260
atggcagagc tgacagctcg aatctcccag ctggagatgg cccgacagaa gaaggagagt   1320
gaggctgtgg agtggcagca gaaggcccag atggtacagg aagacttgga gaagacccgt   1380
gctgagctga agactgccat gagtacacct catgtgcag agcctgctga gaatgagcag   1440
gatgagcagg atgagaatgg ggcagaggct agtgctgacc tacgggctga tgctatggcc   1500
aaggaccgca gtgaggagga acgtaccact gaggcagaga agaatgagcg tgtgcagaag   1560
cacctgaagg ccctcacttc ggagctggcc aatgccagag atgagtccaa gaagactgcc   1620
aatgacatga tccatgctga gaacatgcga ctggccgag acaaatacaa gaccctgcgc   1680
cagatccggc agggcaacac caagcagcgc attgacgaat ttgagtctat gtaa         1734
```

MOESIN MODULATORS AND USES THEREOF

TECHNICAL FIELD

The present application relates generally to the field of molecular biology and medicine. More specifically, the present application concerns methods and compositions for modulating moesin activities and related conditions.

BACKGROUND

Moesin, which stands for membrane-organizing extension spike protein, is a membrane bound intracellular protein initially indentified in bovine uterus and characterized as a possible receptor for heparin. Lankes et al., *Biochem J.* 251:831-42 (1988). Full length native human moesin has 577 amino acids, with a molecular weight of about 75 kD. It shares about 98.3% sequence identity with mouse moesin. Sato et al., *J. Cell Sci.* 103:131-143 (1992).

Further studies have characterized moesin as a member of the ezrin-radixin-moesin (ERM) protein family. These are proteins that are primarily expressed in cytoplasm, concentrated in actin rich cell-surface structures. Sequence and structural analysis of the ERM proteins revealed that they share high degrees of inter-species and inter-molecular homologies. The ERM proteins have three domains: an N-terminal domain called FERM domain (band four-point-one, ezrin, radixin, moesin homology domain) because of its homology with the band 4.1 protein, a central helical domain and a C-terminal tail domain. The C-terminal tail domain binds F-actin while the N-terminal FERM domain is responsible for binding to adhesion molecules in the plasma membrane. Louvet-Vallee (2000).

The functions of ERM proteins are regulated by an intramolecular interaction between the N-terminal FERM domain and the C-terminal tail domain. Pearson et al., Cell 101:259-70 (2000); Louvet-Vallee (2000). The ERM proteins exist in two states in terms of activities: a dormant state and an active state. The active form is involved in intercellular interactions and the dormant form is present in cytoplasm. The difference between these two states depends on the conformation of the protein. In dormant form, the FERM domain is tightly bound to the tail domain, mutually masking the binding sites for other molecules on each domain. The central helical domain serves as a flexible bend to enable the reach and binding of the two terminal domains. Dormant moesin becomes activated when the tightly bound structure opens up, with the FERM domain attaching to the membrane by binding specific membrane proteins and the last 34 residues of the C-terminal tail domain binding to actin filaments.

Within the tail domain, there exists a threonine residue at position 558 of moesin (Thr 558) (position 564 for radixin and 567 for ezrin), whose phosphorylation has been shown to play a key role in the activation of ERM proteins. Pearson et al. (2000). Phosphorylation at Thr 558 weakens the FERM/tail interaction and, in the presence of phospholipids, unmasks the membrane protein and F-actin binding sites on relative domains. In addition, the activated FERM domain also participates in the Rho signaling pathway. Takahashi et al., *J. Biol. Chem.* 272:23371-5 (1997). In moesin, Thr 558 is believed to be phosphorylated by a rho associated coiled coil forming protein kinase (ROCK). Oshiro et al. *J. Biol. Chem.* 273:34663-6 (1998). Other protein kinases known to cause Thr 558 phosphorylation include, but not limited to, PKC, PIP5KIa, P38 and Slik. Hipfner et al., *Genes Dev.* 18:2243-8 (2004).

The presence and functions of moesin and other ERM proteins have been implicated in many physiological as well as pathological conditions. They act as structural linkers between the plasma membrane and the actin cytoskeleton, playing roles in the formation of microvilli, cell-cell adhesion, maintenance of cell shape, cell mobility and membrane trafficking. Later studies have revealed that they are also involved in many signaling pathways including Rho pathway, PI3-kinase/Akt pathway and CD14 pathway. Louvet-Vallee, *Biol. Cell* 92:305-16 (2000); Thome et al., *Infect. Immun.* 67:3215 (1999). Moesin has been suggested to play roles in the growth and metastasis of certain cancers.

Moesin has also been associated with autoimmune diseases. Wagatsuma et al reported detections of anti-ERM autoantibodies in patients with rheumatoid arthritis (RA). Wagatsuma et al., *Mol. Immunol.* 33:1171-6 (1996). Of the 71 patient sera tested, 24 samples (33.8%) reacted with at least one of the recombinant ERM antigens and 10 samples (14%) reacted with recombinant moesin alone. However, the study did not find significant correlation between the presence of anti-ERM antibodies and clinical manifestation, such as disease duration or stage. Moreover, sera from patients with other autoimmune diseases such as Primary Sojgren's Syndrome (PSS) and systemic lupus erythematosus (SLE) did not show any reactivity to the three ERM proteins.

Takamatsu et al reported detection of specific antibodies to moesin in the sera of patients with acquired aplastic anemia (AA). Takamatsu et al., *Blood* 109:2514-20 (2007). Using ELISA, anti-moesin antibodies were shown at high titers in 25 of 67 (37%) AA patients. Further in vitro studies showed that anti-moesin antibodies from AA patients induced inflammatory cytokines such as TNF-α and IFN-γ, implicating its role in the pathophysiology of the disease. Espinoza et al., *Intl. Immu.* 21:913-23 (2009); Takamatsu et al., *J. Immunol.* 182:703 (2009).

Given the complex and important functions of human moesin protein in multiple physiological and pathological settings, it is desirable to explore clinically relevant molecular entities capable of modulating moesin activities, as well as methods of making and using the same. The present application described herein provides these and other benefits.

All references cited herein, including patent applications and publications, are incorporated by reference in their entirety.

DISCLOSURE OF THE INVENTION

The present application provides compositions and methods for modulating moesin activities in vitro or in vivo. In one embodiment, moesin function is modulated through inhibition of moesin activation. A moesin modulator can be used therapeutically for treating disorders and pathological conditions associated with abnormal activation of moesin, such as cancers, fibrosis, and respiratory disorders. In one embodiment, the moesin modulator is an isolated antibody that binds the C-terminal tail domain of human moesin. In one embodiment, binding of the antibody to the moesin tail domain interferes or blocks the phosphorylation of Thr 558 within the tail domain, thereby blocking moesin from being activated.

In one aspect, the moesin modulator comprises a truncated moesin fragment having at least ten contiguous amino acid residues of the C-terminal tail domain of human moesin (SEQ ID NO:1). Such fragment is capable of interfering, by competitive binding, with the interaction of native moesin to its protein kinase for the Thr 558 phosphorylation, thereby blocking the native moesin from being activated.

The amino acid sequence of C-terminal tail domain of human moesin is as follows:

(SEQ ID NO: 1)
HVAEPAENEQDEQDENGAEASADLRADAMAKDRSEEERTTEAEKNERVQK

HLKALTSELANARDESKKTANDMIHAENMRLGRDKYKTLRQIRQGNTKQR

IDEFESM

In one embodiment, the moesin fragment modulator comprises residues surrounding the Thr558 site, such as the sequence GRDKYKTLRQIRQ (SEQ ID NO:2).

In one aspect, the moesin modulator comprises a small molecule compound capable of interfering with the phosphorylation of Thr 558 of human moesin. Such small molecule inhibitor may bind to and block the Thr 558 site directly, or may bind to a position on moesin that causes conformational changes or hindrances, thereby blocking the Thr 558 site from binding to a protein kinase.

In one embodiment, the moesin modulators of the present application interfere with moesin's interaction with its binding partners (e.g., structural proteins or moesin substrates), thereby disrupting moesin's structural roles in cytoskeleton or its signaling pathways.

In one aspect, a moesin modulator of the present application is linked to a toxin such as a cytotoxic agent. These molecules/substances can be formulated or administered in combination with an additive/enhancing agent, such as a radiation and/or chemotherapeutic agent.

The present application also provides methods useful for modulating disease or pathological conditions associated with abnormal activation of moesin. Thus, in one aspect, the present application provides a method of modulating moesin activation in a subject, said method comprising administering to the subject a modulator molecule of the present application that inhibits phosphorylation of Thr 558, whereby moesin activation is modulated.

The moesin is involved in multiple cellular structures and signaling pathways that are important for many biological and physiological functions, including, e.g., cell proliferation, cell survival, cell migration, cell morphogenesis and cell apoptosis. Thus, in another aspect, the present application provides a method of inhibiting moesin activated cell growth (e.g. proliferation and/or survival), said method comprising contacting a cell or tissue with a moesin modulator of the present application, whereby cell proliferation associated with moesin activation is inhibited. In yet another aspect, the present application provides a method of inhibiting moesin activated cell proliferation, said method comprising contacting a cell or tissue with an effective amount of a modulator molecule of the present application, whereby cell proliferation associated with moesin activation is inhibited.

In one embodiment, the present application provides a method of inducing or promoting apoptosis in a cell or tissue, said method comprising contacting a target cell or tissue with an effective amount of a modulator molecule of the present application, thereby inducing or promoting apoptosis of the cell or tissue. Target cells or tissues can be cancerous cells/tissues, epithelial cells/tissues, or endothelial cells/tissues.

In one aspect, the present application provides a method of treating a pathological condition associated with abnormal moesin activation in a subject; said method comprising administering to the subject an effective amount of a modulator molecule of the present application, whereby said condition is treated.

In one aspect, the present application provides a method of therapeutically treating a mammal having a cancerous tumor comprising a cell with abnormal activation of moesin, said method comprising administering to said mammal an effective amount of a modulator molecule of the present application, thereby effectively treating said mammal.

In one aspect, the present application provides a method for treating or preventing a cell proliferative disorder associated with abnormal activation of moesin, said method comprising administering to a subject in need of such treatment an effective amount of an a modulator molecule of the present application, thereby effectively treating or preventing said cell proliferative disorder. In one embodiment, said proliferative disorder is cancer. In yet another embodiment, said proliferative disorder is organ fibrosis such as pulmonary fibrosis, cystic fibrosis, cirrhosis, endomyocardial fibrosis, myelofibrosis, retroperitoneal fibrosis, Crohn's Disease, Keloid, systemic sclerosis or progressive massive fibrosis.

In one embodiment, a cell that is targeted in a method of the present application is a cancer cell. For example, a cancer cell can be one selected from the group consisting of a breast cancer cell, a colorectal cancer cell, a lung cancer cell, a papillary carcinoma cell (e.g., of the thyroid gland), a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a prostate cancer cell, a gastric carcinoma cell, a head and neck squamous carcinoma cell, a melanoma cell and a leukemia cell. In one embodiment, a cell that is targeted in a method of the present application is a hyperproliferative and/or hyperplastic cell. In one embodiment, a cell that is targeted in a method of the present application is a dysplastic cell. In yet another embodiment, a cell that is targeted in a method of the present application is a metastatic cell.

Compositions of the present application can be used in combination with additional therapeutic agents. In one embodiment, the compositions of the present application can be used in combination with one or more cytokines, such as proinflammatory cytokines. Examples of proinflammatory cytokines useful in combination with the compositions of the present application include, but not limited to, TNFs (TNF-alpha and TNF-beta), IL-1 and IL-6. In one embodiment, a method of treatment of the present application further comprises a step wherein a targeted cell and/or tissue (e.g., a cancer cell) is exposed to radiation treatment, a chemotherapeutic agent or other cytotoxic agent.

In one aspect, the present application provides compositions comprising one or more modulator molecules of the present application and a carrier. In one embodiment, the carrier is pharmaceutically acceptable.

BRIEF DESCRIPTION OF THE DRAWINGS

FIG. 1(*a*). Amino acid sequence of the full length human moesin protein (SEQ ID NO: 3).

FIG. 1(*b*). cDNA sequence of the full length human moesin protein (SEQ ID NO: 4), wherein the underline indicates nucleic acid sequence encoding for about the C-terminal tail domain.

FIG. 2(*b*). The restriction and cloning map of pET28a(+).

MODES FOR CARRYING OUT THE INVENTION

Figure 2A:
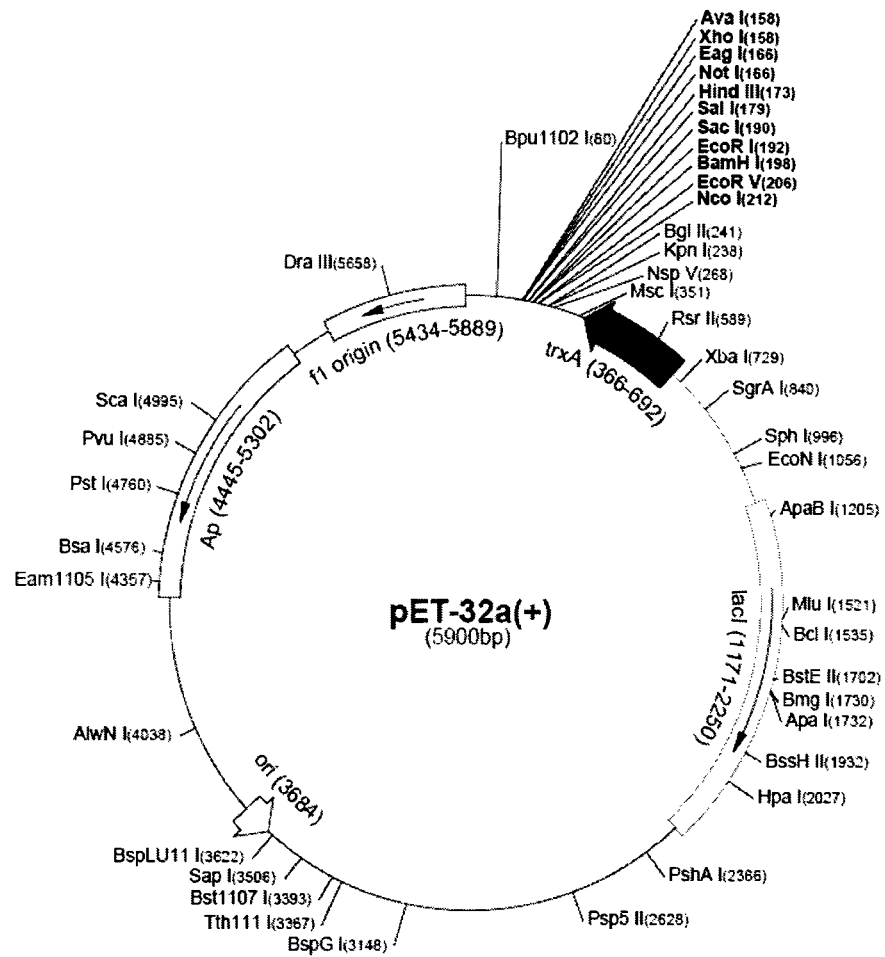
FIG. 2(*a*). The restriction and cloning map of pET32a(+).

The practice of the present application will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" series (Academic Press, Inc.); "Current Protocols in Molecular Biology" (F. M. Ausubel et al., eds., 1987, and periodic updates); "PCR: The Polymerase Chain Reaction", (Mullis et al., eds., 1994). Primers, polynucleotides and polypeptides employed in the present application can be generated using standard techniques known in the art.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Definitions

The term "moesin" stands for membrane-organizing extension pike protein, as described in Lankes and Furthmayr (1991) Proc. Natl. Acad. Sci., 88:8297-8301. Full length human moesin protein is a 577-amino acid polypeptide having the amino acid sequence as set forth in SEQ ID NO:3 (FIG. 1). The moesin protein consists of three domains: the N-terminal FERM domain, the helical domain and the C-terminal tail domain, as further defined below. It belongs to the ERM (ezrin-radixin-moesin) family. The three ERM proteins, primarily expressed in cytoplasm right beneath the plasma membrane, share high degrees of sequence homology and act as linking proteins between the plasma membrane and the actin cytoskeleton. Furthermore, human moesin protein shares high degrees of sequence homology with moesins from other species such as mouse and bovine moesins. Sato et al. (1992) J. Cell Sci. 103:131-143.

The term "truncated moesin fragment" refers to a portion of the moesin polypeptide that is shorter than the full length wild type moesin protein. In particular, the term encompasses polypeptides of ten amino acids or more having amino acid sequences within a particular domain of moesin (N-terminal FERM domain, helical domain or C-terminal tail domain, as further defined below). Useful in the present application are such moesin fragments capable of binding to domain-specific anti-moesin autoantibodies.

The "N-terminal FERM domain" of human moesin protein refers to the globular portion of the wild type human moesin protein structurally proximate to the amino-terminal of the protein and functionally responsible for localizing the protein to the plasma membrane and interacting with adhesion molecules. The FERM domain, which stands for band four-point-one, ezrin, radixin, moesin homology domain because of its homology with the band 4.1 protein, defines members of the band 4.1 superfamily, which includes cytoskeletal proteins such as erythrocyte band 4.1, talin, and the ezrin-radixin-moesin (ERM) protein family, as well as several tyrosine kinases and phosphatases and the tumor suppressor protein merlin. Specifically, the term refers to the first about 297 amino acid residues of the mature form of human moesin protein (e.g., amino acid residues 1-297). In certain literatures, the same domain is also known as N-ERM associated domain (N-ERMAD), which is included in the definition herein. Bretscher et al. (1995) Biochem. 34, 16830-7.

The "C-terminal tail domain" of human moesin protein refers to the portion of the wild type human moesin protein structurally proximate to the carboxy-terminal of the protein and functionally responsible for binding to and interacting with actin filaments. The tail domain of moesin is positively charged and adopts an extended, meandering structure. Specifically, the term refers to the last about 107 amino acid residues of human moesin protein (e.g., amino acid residues 471-577). In certain literatures, the same domain is also known as C-ERM associated domain (C-ERMAD), which is included in the definition herein. Bretscher et al. (1995). The last 34 amino acid residues of the C-terminal tail domain are highly conserved amongst ERM proteins and forms the region for binding to F-actin. Within the F-actin binding region, there exists a threonine residue (Thr558 in wild type human moesin) that is phosphorylated during the activation of the protein.

The "helical domain" of human moesin protein refers to the central portion of the wild type human moesin resided in between the N-terminal FERM domain and the C-terminal tail domain. It adopts an extended alpha-helical structure, acting as a linker between the two terminal domains. Specifically the term refers to the region encompassing about amino acid residues 298-470 of human moesin protein.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

"Disorder or pathological conditions associated with abnormal moesin activation" refers to disorders or conditions either caused or facilitated by abnormal activation of moesin in a subject. Abnormal activation of moesin, which is at least partially due to the phosphorylation of Thr 558 within the C-terminal tail domain of the moesin protein, has been implicated in disease processes and conditions involving abnormal epithelial or endothelial cells. Exemplary pathological conditions associated with abnormal moesin activation include, but not limited to, tumor growth and metastasis, fibrosis of organs and tissues, pulmonary artery hypertension, and inflammations.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

An "autoimmune disorder" or "autoimmune disease" herein is a disease or disorder arising from an immune response directed against an individual's own substances and tissues. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE) (including but not limited to lupus nephritis, cutaneous lupus); diabetes mellitus (e.g. Type I diabetes mellitus or insulin dependent diabetes mellitis); multiple sclerosis; Reynaud's syndrome; autoimmune thyroiditis; Hashimoto's thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (YIP) or autoimmune thrombocytopenia etc.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the present application are used to delay development of a disease or disorder.

An "effective amount" refers to an amount effective, at dosages and for periods of time necessary, to achieve the desired therapeutic or prophylactic result.

A "therapeutically effective amount" of a substance/molecule of the present application, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutically acceptable" as used herein refers to any component (e.g., saline, solvents, dispersion media, coatings, antibacterial and antifungal agents, isotonic and absorption delaying agents) that is compatible with pharmaceutical administration.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin;

spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; other antiandrogens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-1H-pyrazol-1-yl) benzenesulfonamide; and pharmaceutically acceptable salts, acids or derivatives of any of the above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-.alpha. and -.beta.; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-.alpha., -.beta., and -.gamma.; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-.alpha. or TNF-.beta.; and other polypeptide factors including LIF and kit ligand (KL). As used herein, the term cytokine includes proteins from natural sources or from recombinant cell culture and biologically active equivalents of the native sequence cytokines. As a subset of cytokine, "proinflammatory cytokine" refers to cytokines that induce or promote inflammatory reactions. Examples of proinflammatory cytokines include TNF-alpha, TNF-beta, IL-1 and IL-6.

An "isolated" polypeptide is one that has been identified and separated and/or recovered from a contaminant component of its natural environment. Contaminant components of its natural environment are materials that would interfere with diagnostic or therapeutic uses for the polypeptide, and may include enzymes, hormones, and other proteinaceous or non-proteinaceous solutes. In certain embodiments, the polypeptide will be purified (1) to greater than 95% by weight of polypeptide as determined by the Lowry method, or more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue, or silver stain. Isolated polypeptide includes the polypeptide in situ within recombinant cells since at least one contaminant component of the polypeptide's natural environment will not be present. Ordinarily, however, isolated polypeptide will be prepared by at least one purification step.

The term "antibody" is used in the broadest sense and specifically covers monoclonal antibodies (including full length or intact monoclonal antibodies), polyclonal antibodies, multivalent antibodies, multispecific antibodies (e.g., bispecific antibodies) formed from at least two intact antibodies, and antibody fragments (see below) so long as they exhibit the desired biological activity.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. Monoclonal antibodies are highly specific, being directed against a single antigen. In certain embodiments, a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of the present application. In contrast to polyclonal antibody preparations that typically include different antibodies directed against different determinants (epitopes), each monoclonal antibody is directed against a single determinant on the antigen. In addition to their specificity, monoclonal antibody preparations are advantageous in that they are typically uncontaminated by other immunoglobulins.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

The term "biological activity" and "biologically active" with regard to a polypeptide of the present application refer to the ability of a molecule to specifically bind to and regulate cellular responses, e.g., proliferation, migration, etc. Cellular responses also include those mediated through a receptor, including, but not limited to, migration, and/or proliferation. In this context, the term "modulate" includes both promotion and inhibition.

Responsiveness of a patient can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesion size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) relief, to some extent, of one or more symptoms associated with the disorder; (7) increase in the length of disease-free presentation following treatment; (8) decrease of auto-immune response, which may, but does not have to, result in the regression or ablation of the disease lesion, e.g., progression-free survival; (9) increased overall survival; (10) higher response rate, and/or (11) decreased mortality at a given point of time following treatment.

The term "benefit" is used in the broadest sense and refers to any desirable effect.

The present application provides compositions and methods for modulating moesin activities and for treating disorders associated with dysfunction of epithelial cells. Conventional methods known to the skilled in the art can be used to carry out the present application.

Modulators of Moesin Activity

Modulators of moesin activities include those that mimic or enhance one or more biological activities of moesin (agonists) and those that prevent or interfere with the effect of moesin (antagonists or inhibitors). In one aspect, the moesin modulators described herein are moesin inhibitors. Any molecule that disrupts moesin activities can be a candidate inhibitor. Screening techniques well known to those skilled in the art can identify these molecules. One way to inhibit moesin is to interfere with its activation by blocking the phosphorylation of the dormant form or by dephosphorylating the active form. In one embodiment, such disruption of moesin phosphorylation is accomplished at the Thr 558 site within the C-terminal tail domain. "Moesin phosphorylation inhibitor" includes any molecule that partially or fully blocks, inhibits, or interferes with the phosphorylation site(s) on moesin. Examples of such inhibitors include, but not limited to: (1) small organic and inorganic compounds, (2) small peptides, (3) antibodies and derivatives, (4) peptides closely related to moesin or other ERM family proteins, and (5) nucleic acid aptamers.

1. Small Molecule Modulators

Small molecules can be useful modulators of moesin activities. Examples of small molecule modulators include small peptides, peptide-like molecules, and synthetic, non-peptidyl organic or inorganic compounds. In one aspect, a small molecule modulator of the present application is soluble. A "small molecule" refers to a composition that has a molecular weight of less than about 5 kD, or less than about 0.6 kD. Small molecules can be nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays. Examples of methods for the synthesis of molecular libraries have been described (Carell et al., Angewandte Chemie International Edition. 33:2059-2061 (1994); Carell et al., Angewandte Chemie International Edition. 33:2061-2064 (1994); Cho et al., Science. 261:1303-5 (1993); DeWitt et al., Proc Natl Acad Sci USA. 90:6909-13 (1993); Gallop et al., J. Med. Chem. 37:1233-51 (1994); Zuckermann et al., J. Med. Chem. 37:2678-85 (1994).

2. Polypeptide/Antibody Modulators

In one embodiment, the moesin modulators provided herein can be polypeptide compositions. Polypeptides that inhibit moesin activation are potentially useful inhibitors. In one embodiment, the polypeptide moesin inhibitors are anti-moesin antibodies specific to the C-terminal tail domain of the moesin protein. They may prevent moesin from being activated by blocking the phosphorylation site at Thr 558 of the tail domain. In another embodiment, the polypeptide moesin inhibitors are truncated, non-functional fragments of the C-terminal tail domain that include the Thr 558 phosphorylation site. Such fragments may compete for phosphorylation at Thr 558 with endogenous moesin molecules, thereby preventing or reducing them from being activated. In one aspect, the polypeptide moesin inhibitor comprises at least ten contiguous amino acid residues from the region surrounding the Thr 558 site. For example, the polypeptide may comprise partial or complete sequence of GRDKYKTLRQIRQ (SEQ ID NO:2).

In one embodiment, the polypeptide modulators can be isolated from cells or tissue sources by an appropriate purification scheme using standard protein purification techniques. In another embodiment, the modulators are produced by recombinant DNA techniques. Alternative to recombinant expression, modulators can be synthesized chemically using standard peptide synthesis techniques.

Polypeptide moesin modulators include mutant or variant proteins, any of which residues may be changed from the corresponding residues of these peptides, while still encoding a peptide that maintains modulatory activity. In one embodiment, a variant of a reference polypeptide has at least 50%, 60%, 70%, 80%, 90%, 95%, 98%, 99% amino acid sequence identity with the sequence of a reference polypeptide. In general, the variant exhibits substantially the same or greater binding affinity than the reference polypeptide, e.g., at least 0.75×, 0.8×, 0.9×, 1.0×, 1.25× or 1.5× folds of the binding affinity of the reference polypeptide, based on an art-accepted binding assay quantitation unit/metric.

Human and non-human polyclonal and monoclonal antibodies (including humanized forms of non-human monoclonal antibodies), which modulate the biological properties of moesin, are contemplated in the present application. These include amino acid sequence variants, glycosylation variants and fragments of antibodies. Antibody modulators or variants thereof can be made using technologies known in the art and described briefly herein. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The antibodies of the present application can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In one embodiment, moesin inhibitors are screened and identified by a high throughput competition assay, wherein the candidate compound's ability to compete with moesin's binding to its binders (e.g., anti-moesin antibodies or kinases acting on the phosphorylation site of moesin) is measured. A cell-free assay comprises contacting moesin or truncated moesin fragment with a known binder compound to form an assay mixture, contacting the assay mixture with a test compound, and determining the ability of the test compound to interact with moesin or the binder compound, where determining the ability of the test compound to interact with moesin or the binder compound comprises determining whether a detectable characteristic of moesin/binder complex is modulated. For example, the binding interaction of moesin and a protein kinase, as determined by the extent of phosphorylation of the protein, can be indicative of whether the test compound is able to modulate the interaction between moesin and the kinase compound. Amount of complex can be assessed by methods known in the art, for example ELISA (including competitive binding ELISA), yeast two-hybrid and proximity (e.g., fluorescent resonance energy transfer, enzyme-substrate) assays.

Recombinant Production of Peptide or Polypeptide

The polypeptides of the present application can be produced recombinantly, using techniques and materials readily obtainable. For recombinant production of a polypeptide of the present application, the nucleic acid encoding it is isolated and inserted into a replicable vector for further cloning (amplification of the DNA) or for expression. DNA encoding the polypeptide of the present application is readily isolated and sequenced using conventional procedures. For example, a DNA encoding a human moesin protein is isolated and sequenced, e.g., by using oligonucleotide probes that are capable of binding specifically to genes encoding the protein. Many vectors are available. The vector components generally include, but are not limited to, one or more of the following: a signal sequence, an origin of replication, one or more selection genes, an enhancer element, a promoter, and a transcription termination sequence.

Polypeptides of the present application may be produced recombinantly not only directly, but also as a fusion polypeptide with a heterologous polypeptide, which is typically a signal sequence or other polypeptide having a specific cleavage site at the N-terminus of the mature protein or polypeptide. The heterologous signal sequence selected typically is one that is recognized and processed (i.e., cleaved by a signal peptidase) by the host cell. For prokaryotic host cells, the signal sequence can be a prokaryotic signal sequence selected, for example, from the group of the alkaline phosphatase, penicillinase, 1pp, or heat-stable enterotoxin II leaders. For yeast secretion the native signal sequence can be, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

The DNA for such precursor region is ligated in reading frame to DNA encoding the polypeptide of the present application. Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, typically primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding a polypeptide of the present application, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid Yrp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

Expression and cloning vectors usually contain a promoter that is recognized by the host organism and is operably linked to a nucleic acid encoding a polypeptide of the present application. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the polypeptide of the present application.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldyhyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription of polypeptides of the present application from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and typically Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the rous sarcoma virus long terminal repeat can be used as the promoter.

Transcription of a DNA encoding a polypeptide of the present application by higher eukaryotes is often increased by inserting an enhancer sequence into the vector. Many enhancer sequences are now known from mammalian genes (globin, elastase, albumin, α-fetoprotein, and insulin). Typically, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is typically located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide of the present application. One useful transcription termination component is the bovine growth hormone polyadenylation region. See WO94/11026 and the expression vector disclosed therein.

Suitable host cells for cloning or expressing DNA encoding the polypeptides of the present application in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Typically, the *E. coli* cloning host is *E. coli* 294 (ATCC 31,446), although other strains such as *E. coli* B, *E. coli* BL21(DE3), *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide of the invention-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244, 234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of polypeptides of the present application can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogasteri* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present application, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for polypeptide of the present application production and cultured in conventional nutrient media modified as appropriate for inducing promoters, selecting transformants, or amplifying the genes encoding the desired sequences.

The host cells used to produce polypeptides of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Chemical Synthesis of Peptide or Polypeptide

The peptides of the present application can also be produced by chemical synthesis, for example, the solid phase synthesis method described by Merrifield in J.A.C.S. 85: 2149-2154 (1963) or the standard solution synthesis method described in "Peptide Synthesis" by Bodanszky, et al, second edition, John Wiley and Sons, 1976. These books are entirely incorporated herein by reference.

The general procedure of the solid phase method of synthesis of a peptide involves initially attaching the protected C-terminal amino acid of the peptide to the resin. After attachment the resin is filtered, washed and the protecting group (e.g. t-butyloxycarbonyl) on the alpha amino group of the C-terminal amino acid is removed. The removal of this protecting group must take place, of course, without breaking the bond between that amino acid and the resin. To the resulting resin peptide is then coupled the penultimate C-terminal protected amino acid. This coupling takes place by the formation of an amide bond between the free carboxy group of the second amino acid and the amino group of the first amino acid attached to the resin. This sequence of events is repeated with successive amino acids until all amino acids of the peptide are attached to the resin. Finally, the protected peptide is cleaved from the resin and the protecting groups removed to obtain the desired peptide. The cleavage techniques used to separate the peptide from the resin and to remove the protecting groups depend upon the selection of resin and protecting groups and are known to those familiar with the art of peptide synthesis.

The resin mentioned above may be any suitable polymer and shall contain a functional group to which the first protected amino acid can be firmly linked by a covalent bond. Various polymers are suitable for this purpose, such as cellulose, polyvinyl alcohol, polymethylmethacrylate, and polystyrene. Appropriate protecting groups usable in solid phase synthesis include t-butyloxycarbonyl (BOC), benzyl (BZL), t-amyloxycarbonyl (AOC), tosyl (TOS), o-bromophenylmethoxycarbonyl (BrZ), 2,6-dichlorobenzyl (BZLC1.sub.2), and phenylmethoxycarbonyl (Z or CBZ). Additional protecting groups are also described in J. F. W. McOmie, "Protective Groups in Organic Chemistry", Plenum Press, New York, 1973. This book is entirely incorporated herein by reference.

The standard solution synthesis method can be performed by either stepwise or block coupling of amino acids or peptide fragments using chemical or enzymatic methods of amide bond formation. These solution synthesis methods are well known in the art.

Polypeptide Purification

A polypeptide or protein of the present application may be recovered from a subject. When using recombinant techniques, a polypeptide of the present application can be produced intracellularly, in the periplasmic space, or directly secreted into the medium. Polypeptides of the present application may be recovered from culture medium or from host cell lysates. If membrane-bound, it can be released from the membrane using a suitable detergent solution (e.g. Triton-X 100) or by enzymatic cleavage. Cells employed in expression of a polypeptide of the present application can be disrupted by various physical or chemical means, such as freeze-thaw cycling, sonication, mechanical disruption, or cell lysing agents.

If a peptide is chemically synthesized, the peptide of the present application may be recovered from the reaction medium by any suitable techniques capable of separating the desired peptide from other components in the medium. For a solid phase synthesis, the protected peptide is firstly cleaved off the resin using a suitable cleaving solution. The selection of cleaving solution depends upon the properties of the resin and the amino acid bound thereto (such as trifluoroacetic acid for FMOC method). Cleaving is usually carried out under acid condition. Upon completion of cleaving, a dissociative peptide is then obtained and further purified using any suitable techniques (such as the methods described below).

The following procedures are exemplary of suitable protein purification procedures: by fractionation on an ion-exchange column; ethanol precipitation; reverse phase HPLC; chromatography on silica, chromatography on heparin SEPHAROSE™ chromatography on an anion or cation exchange resin (such as a polyaspartic acid column, DEAE, etc.); chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of polypeptides of the present application. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular polypeptide of the present application produced.

Therapeutic/Prophylactic Applications

Moesin modulators of the present application can be used therapeutically for modulating cellular activities in vitro or in vivo. In one aspect, moesin inhibitors can be used for blocking moesin from being activated, thereby treating disorders associated with abnormal activation of moesin.

In one aspect, the present application provides a method for inhibiting proliferation of abnormal epithelial or endothelial cells in a subject having a disorder associated with abnormal activation of moesin. In another aspect, the present application provides a method for inducing or promoting apoptosis of abnormal epithelial or endothelial cells in a subject having a disorder associated with abnormal activation of moesin.

It is contemplated that the composition of the present application may be used to treat a mammal. In one embodiment, the composition is administered to a nonhuman mammal for the purposes of obtaining preclinical data, for example. Exemplary nonhuman mammals to be treated include nonhuman primates, dogs, cats, rodents and other mammals in which preclinical studies are performed. Such mammals may be established animal models for a disease to be treated with the composition or may be used to study toxicity of the composition of interest. In each of these embodiments, dose escalation studies may be performed in the mammal.

In addition, or in the alternative, the composition is used to treat a human, e.g. a patient suffering from a disease or disorder who could benefit from administration of the composition.

In one embodiment, the present application encompasses treatment of proliferative disorder associated with abnormal moesin activation. Because abnormal cell proliferation is involved in both primary tumor growth and metastasis, the treatment provided by the present application is capable of inhibiting the neoplastic growth of tumor at the primary site as well as preventing metastasis of tumors at the secondary sites, therefore allowing attack of the tumors by other therapeutics. Examples of cancer to be treated herein include, but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. More particularly, cancers that are amenable to treatment by the antibodies of the present application include breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, melanoma, ovarian cancer, mesothelioma, and multiple myeloma.

Pharmaceutical Formulations

Various substances or molecules (including peptides, etc.) may be employed as therapeutic agents. These substances or molecules can be formulated according to known methods to prepare pharmaceutically useful compositions, whereby the product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

It is contemplated that when used to treat various diseases such as tumors, the modulators of the present application can be combined with other therapeutic agents suitable for the same or similar diseases. When used for treating cancer, modulators of the present application may be used in combination with conventional cancer therapies, such as surgery, radiotherapy, chemotherapy or combinations thereof.

In some other aspects, other therapeutic agents useful for combination tumor therapy with the moesin antagonist of the present application include antagonists of other factors that are involved in tumor growth, such as EGFR, ErbB2 (also known as Her2) ErbB3, ErbB4, or TNF. Preferably, the anti-NRP1 antibody of the present application can be used in combination with small molecule receptor tyrosine kinase inhibitors (RTKIs) that target one or more tyrosine kinase receptors such as VEGF receptors, FGF receptors, EGF receptors and PDGF receptors. Many therapeutic small molecule RTKIs are known in the art, including, but are not limited to, vatalanib (PTK787), erlotinib (TARCEVA®), OSI-7904, ZD6474 (ZACTIMA®), ZD6126 (ANG453), ZD1839, sunitinib (SUTENT®), semaxanib (SU5416), AMG706, AG013736, Imatinib (GLEEVEC®), MLN-518, CEP-701, PKC-412, Lapatinib (GSK572016), VELCADE®, AZD2171, sorafenib (NEXAVAR®), XL880, and CHIR-265.

The moesin modulators of the present application, either alone or in combination with a second therapeutic agent can be further used in combination with one or more chemotherapeutic agents. A variety of chemotherapeutic agents may be used in the combined treatment methods of the present application. An exemplary and non-limiting list of chemotherapeutic agents contemplated is provided herein under "Definition."

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present application may vary depending on the particular use envisioned. The determination of the appropriate dosage or route of administration is well known within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a substance or molecule of the present application is employed, normal dosage amounts may vary from about 10 ng/kg to up to 100 mg/kg of mammal body weight or more per day, preferably about 1 mg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a substance or molecule is desired in a formulation with release characteristics suitable for the treatment of any disease or disorder requiring administration of the substance or molecule, microencapsulation of the substance or molecule is contemplated. Microencapsulation of recombinant proteins for sustained release has been successfully performed with human growth hormone (rhGH), interferon- (rhIFN—), interleukin-2, and MN rgp120. Johnson et al., Nat. Med., 2:795-799 (1996); Yasuda, Biomed. Ther., 27:1221-1223 (1993); Hora et al., Bio/Technology, 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439462; WO 97/03692, WO 96/40072, WO 96/07399; and U.S. Pat. No. 5,654,010.

The sustained-release formulations can be developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 1-41.

The compositions (e.g., pharmaceutical compositions) can be included in a kit, container, pack, or dispenser together with instructions for administration. When supplied as a kit, the different components of the composition may be packaged in separate containers and admixed immediately before use. Such packaging of the components separately may permit long-term storage without losing the active components' functions. Kits may also include reagents in separate containers that facilitate the execution of a specific test, such as diagnostic tests or tissue typing.

The reagents included in kits can be supplied in containers of any sort such that the life of the different components are preserved and are not adsorbed or altered by the materials of the container. For example, sealed glass ampules may contain lyophilized modulator substance/molecule and/or buffer that have been packaged under a neutral, non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include simple bottles that may be fabricated from similar substances as ampules, and envelopes, that may consist of foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

Kits may also be supplied with instructional materials. Instructions may be printed on paper or other substrate, and/or may be supplied as an electronic-readable medium, such as a floppy disc, CD-ROM, DVD-ROM, Zip disc, videotape, laserdisc, audio tape, etc. Detailed instructions may not, be physically associated with the kit; instead, a user may be directed to an Internet web site specified by the manufacturer or distributor of the kit, or supplied as electronic mail.

In another embodiment of the present application, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The following examples are included to demonstrate preferred embodiments of the present application. It should be appreciated by those of skill in the art that the techniques disclosed in the examples that follow represent techniques discovered by the inventors to function well in the practice of the present application, and thus can be considered to constitute preferred modes for its practice. However, those of skill in the art should, in light of the present disclosure, appreciate that many changes can be made in the specific embodiments that are disclosed and still obtain a like or similar result without departing form the spirit and scope of the present application.

EXAMPLES

Example 1

Preparation of the Anti-Moesin Antibodies

Monoclonal antibody against the C-terminal tail domain of moesin was prepared by using the conventional hybridoma methods. To generate the C-terminal domain having the sequence of SEQ ID NO:1, PCR was used to amplify cDNA fragments corresponding to the C-terminal tail domain as described above (see SEQ ID NO:4 shown in FIG. 1, wherein the underlined portion is the cDNA sequence of the C-terminal tail domain).

Figure 2B:
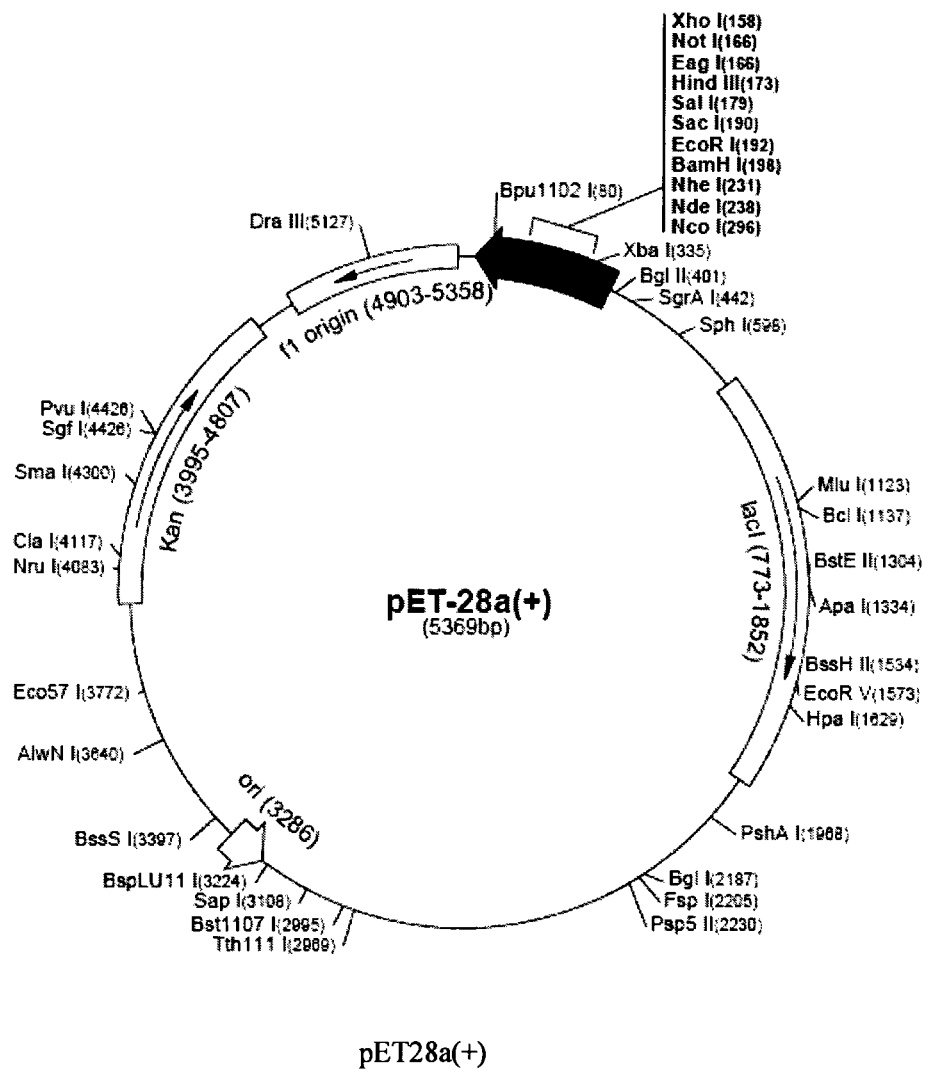

PCR-amplified moesin DNA fragments were cloned into expression vectors selected from pET32a(+) and pET28a(+). The constructed vectors were then used to transform E. coli host cell line BL21(DE3) for culturing and expression. The restriction and cloning maps of pET32a(+) and pET28a(+) are shown in FIGS. 2(a) and 2(b), respectively. The constructed expression systems for the C-terminal domain were verified with restriction enzyme digestion followed by sequencing to confirm the correct reading frame for expression of the C-terminal domain.

After sufficient culturing, host cells with expressed C-terminal domain were harvested for collection and purification of the C-terminal domain according to standard protein expression protocols. The resulting protein fragments were assayed with SDS-PAGE to confirm their identity and purity.

The expressed C-terminal domain was then used to make the monoclonal antibody against the C-terminal tail domain of moesin according to hybridoma methods by using BALB/C mice.

Hybridoma methods were first described by Kohler and Milstein, Nature, 256:495 (1975), which is incorporated into the present application in its entirety for reference. In typical hybridom methods, mice (e.g. BALB/C mice) are immunized with an antigen (e.g. C-terminal domain) and spleen cells from the immunized mice are then fused with myeloma cells. The fused cells are harvested in a medium which selectively allows growth of hybridomas, and viable hybridoma colonies are grown out. After a sufficient time, supernatants are screened by ELISA testing and immunohistochemical assays using the antigen (e.g. C-terminal domain). Positive cells are selected for further sub-cloning. Selected clones are sub-cloned by limited dilution. Sub-cloning is performed until all clones are ELISA-positive. The positive clones are then selected to obtain hybridomas generating monoclonal antibodies against the antigen.

The antibody against full length moesin protein was commercially obtained from Becton, Dickinson and Company, and it also can be produced according to hybridoma methods as described above by using full length moesin protein instead of C-terminal domain.

Example 2

Assessing Moesin Inhibitor's Ability to Inhibit Cell Proliferations

This experiment is used to assess moesin inhibitor's ability to inhibit or reduce cell proliferation.

Cell proliferation assay were performed using a human pulmonary microvascular endothelial cell line (HPMEC). Cells were plated in each well on a 6-well plate at $10^6$ cells/$cm^2$, and cultured at room temperature in the presence of various testing and control reagents as described below. After culturing for a determined period of time, cells were collected and labeled for flow cytometry analysis. Proliferation rates at 2 hrs, 24 hrs and 36 hrs were determined by dividing the mean $OD_{570}$ value from the tested groups with the mean $OD_{570}$ value from the group having the same number of cells as the test groups at the beginning of the cell culturing.

Tested and control groups are as follows:
1) TNF-alpha alone;
2) Antibody against full length moesin protein (anti-Moesin);
3) Antibody against the C-terminal tail domain only (anti-M3);
4) TNF-alpha+anti-Moesin;
5) TNF-alpha+anti-M3;
6) PBS solution (negative control)

Figure 3:
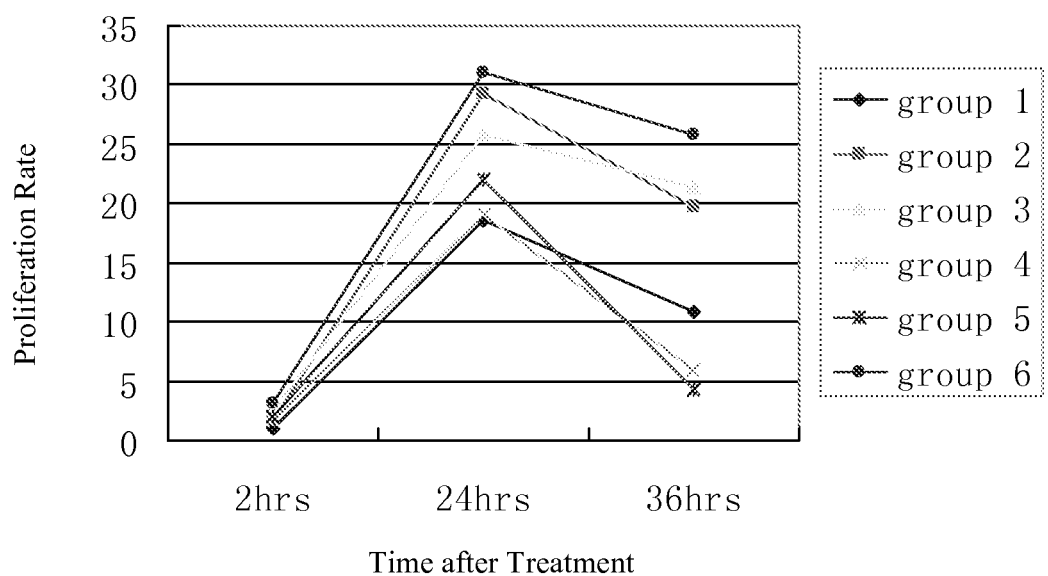
FIG. 3. Graph illustrating the proliferation rate of HPMEC cells after treatment with TNF-alpha (Group 1), antibody against full length moesin (Group 2), antibody against the C-terminal tail domain of the moesin protein (Group 3), TNF-alpha and antibody against full length moesin (Group 4), TNF-alpha and antibody against the C-terminal tail domain of the moesin protein (Group 5), and PBS solution (Group 6).

The resulting cells and supernatant after the culturing were subject to cell morphology analysis, western blot, as well as flow cytometry and immunofluorescence assays. Effects of various agents, particularly the anti-M3 antibody, were examined and characterized. The results are shown in FIG. 3. The proliferation rates of the cells started to drop at around 24 hours after the culturing. When compared with the negative control (Group 6), treatment with anti-moesin and anti-M3 reduced cell proliferation rates, and treatment with anti-moesin and anti-M3 in combination with TNF-alpha reduced cell proliferation rates even more substantially. Treatment with TNF-alpha alone reduced cell proliferation rates but not as much as in combination with anti-moesin or anti-M3. The results indicate that anti-moesin and anti-M3 can inhibit cell proliferation.

Example 3

Analysis of Intercellular Expression of Moesin and Apoptosis

Cell cultures in the presence of anti-moesin antibodies as described in Example 1 were subjected to apoptosis assay as well as surface antigen assay, to assess the antibody's effect on promoting endothelial cell apoptosis and on intercellular expression of moesin (indicating the active form of the protein).

Figure 4A:
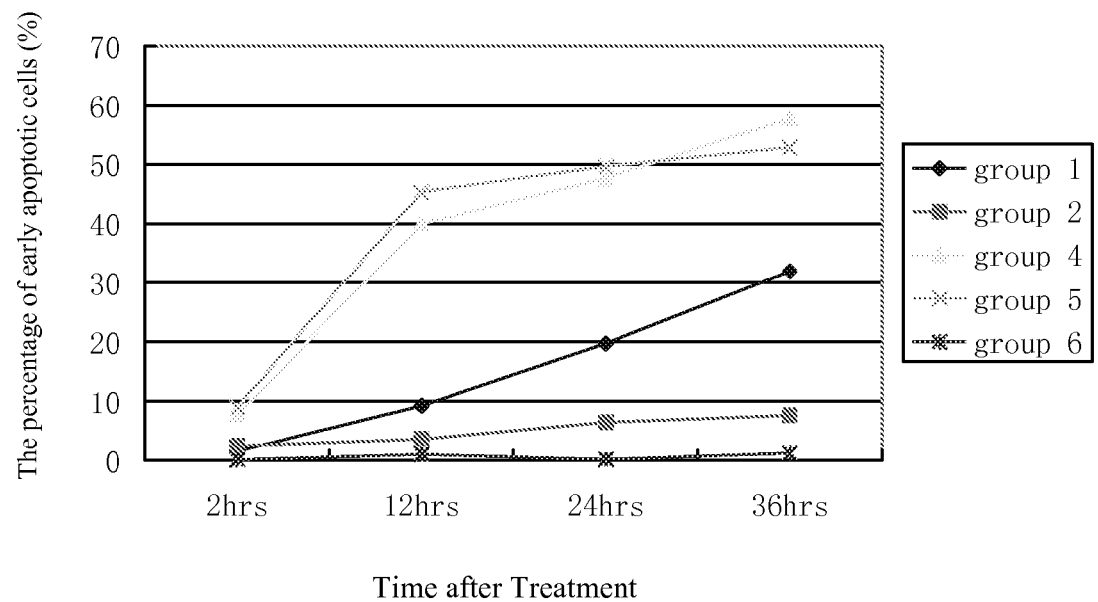
FIG. 4(a) Graph illustrating the early apoptosis of HPMEC cells after treatment with Groups 1-6.
Figure 4B:
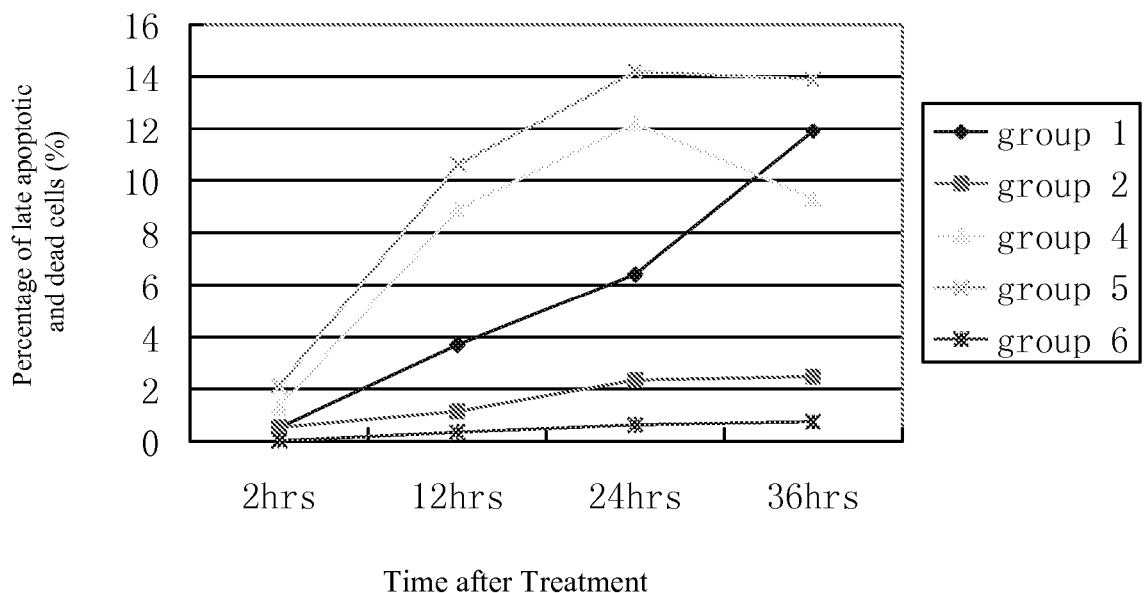
FIG. 4(b) Graph illustrating the late apoptosis and dead HPMEC cells after treatment with Groups 1-6.

Annexin V assay was used to study apoptosis. Collected cells were washed with PBS, centrifuged, and added sequentially with 70% ethanol, RNAs (200 mg/l) and PI (20 mg/l). Cells were then stained with Annexin-V FITC/PI kit for double staining of FITC and PI, because viable cells are both FITC and PI negative, while cells that are in early apoptosis are FITC positive but PI negative, and cells that are in late apoptosis or already dead are both FITC and PI positive. Stained cells are analyzed using a flow cytometer for amount of apoptotic cells in the presence of variant testing agents. The percentage of cells in early apoptosis and the percentage of cells in late apoptosis or dead cells after treatment with the test groups and the control group were determined and the results are shown in FIG. 4(a) and FIG. 4(b) respectively. The results show that treatment with anti-moesin slightly increases the percentages of cells in early apoptosis and cells in late apoptosis or dead. TNF-alpha could substantially enhance the apoptosis-inducing effect of anti-moesin and anti-M3. TNF-alpha alone could induce cell apoptosis but the effect is not as much as it in combination with anti-moesin or anti-M3.

Immunofluorescence assay were used to detect cell surface expression of moesin. HPMEC cells were treated with 0.05% tripsin/0.02% EDTA, after which anti-moesin antibodies were added, and cells were cultured before a fluorescence-labeled secondary antibody was added. Cells were studied under a fluorescence microscope for presence of moesin on cell surface. Cell cultures without the anti-moesin antibody were used as negative control.

The results of the above assays showed that without the anti-moesin antibody, there were no cell surface moesin can be detected. Western blot did not detect any moesin in the supernatant either. In the presence of anti-moesin antibody but without the stimulating factor TNF-alpha, no apparent changes in cytoskeleton, nor significant increase in apoptosis. But after adding TNF-alpha, both apoptosis and cell surface moesin were increased comparing to control group.

Example 4

Observing Impacts of Moesin Inhibitors on Cell's Morphological Changes

Cells were studied under microscope for morphological changes in the presence of various testing agents as described in Example 1.

Cytoskeleton Morphology:

In the control Group 6, cytoskeleton structure appeared normal, with defined cell edges regular pattern, and normal nuclei sizes.

In groups while only anti-moesin antibodies (Group 2 with anti-Moesin and Group 3 with anti-M3) were added, cells appeared normal initially, with partial disrupted F-actin structure and irregular edges seen only after 36 hours incubation. No apparent change in nuclei.

Similar to Group 2, the TNF-alpha only group (Group 1) had no apparent change in structure, until after 36 hrs, when partial disruption of F-actin structure was observed. No apparent change in nuclei.

In groups treated with both TNF-alpha and anti-moesin antibodies, however, the cytoskeleton collapsed after 24 hours, with F-actins spread throughout cytoplasm, forming fibrous bundles composed of non-polar actin filaments. At 36 hours, nuclei condensation can be seen, indicating apoptosis process.

Microvilli Morphology

Figure 5A:
FIG. 5(a) Electronic microscopic picture (×6000) of HPMEC control cells incubated for 36 hours.
Figure 5B:
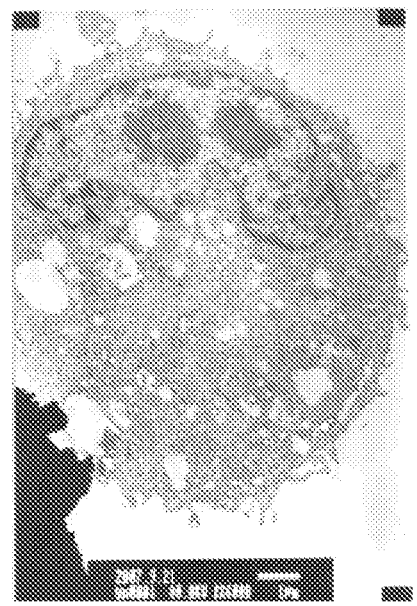
FIG. 5(b) Electronic microscopic picture (×6000) of HPMEC cells treated with TNF-alphah alone for 36 hours.
Figure 5C:
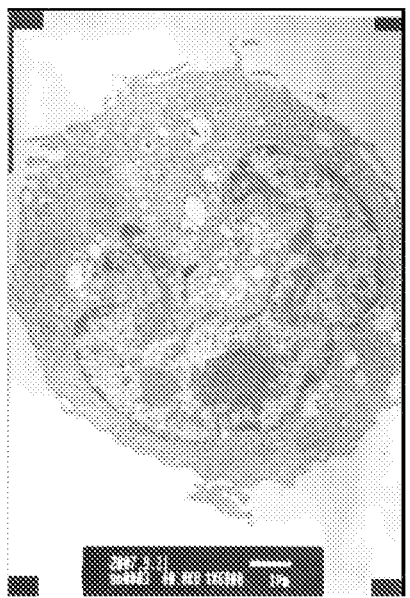
FIG. 5(c) Electronic microscopic picture (×6000) of HPMEC cells treated with TNF-alpha and antibody against full length Moesin for 36 hours.

Normal HPMECs have smooth, cylinder-shaped and regularly patterned microvilli on surface as shown in FIG. 5(a). After 36 hours with TNF-alpha (Group 1), these microvlli appeared to become smaller and less densed as shown in FIG. 5(b). After 36 hours with TNF-alpha plus anti-moesin antibodies (Groups 4 and 5), there were significant reduction or even complete disappearance of microvilli on HPMEC surface as shown in FIG. 5(c).

Our results suggest that anti-moesin antibodies as moesin inhibitors can cause disruption of cell structure and even cell death. But these effects are limited without the inflammatory factors such as TNF-alpha. In the presence of TNF-alpha, however, such damaging effects to the cells are significantly augmented.

What is claimed is:

1. A composition comprising a moesin inhibitor capable of inhibiting the activation of human moesin, wherein the moesin inhibitor consists of a truncated moesin fragment having ten contiguous amino acid residues of the last 34 amino acid residues of the C-terminal tail domain of human moesin as set forth in SEQ ID NO:1; and wherein the truncated moesin fragment comprises the phosphorylation site Threonine 558.

2. The composition of claim 1, which is capable of competing for the phosphorylation of Threonine 558 with full length human moesin.

3. The composition of claim 1, which inhibits proliferation of epithelial or endothelial cells.

4. The composition of claim 1, which promotes apoptosis of epithelial or endothelial cells.

5. A pharmaceutical composition useful for treating a disorder or pathological condition associated with abnormal moesin activation in a subject, comprising a composition of claim 1 and a carrier.

6. The pharmaceutical composition of claim 5, further comprising a second therapeutic agent.

7. A composition comprising a moesin inhibitor capable of inhibiting the activation of human moesin, wherein the moesin inhibitor consists of at least ten contiguous amino acid residues of the sequence GRDKYKTLRQIRQ as set forth in SEQ ID NO:2.

8. The composition of claim 7, which is capable of competing for the phosphorylation of Threonine 558 with full length human moesin.

9. The composition of claim 7, which inhibits proliferation of epithelial or endothelial cells.

10. The composition of claim 7, which promotes apoptosis of epithelial or endothelial cells.

11. A pharmaceutical composition useful for treating a disorder or pathological condition associated with abnormal moesin activation in a subject, comprising a composition of claim 7 and a carrier.

* * * * *